United States Patent [19]

Lafargue et al.

[11] Patent Number: 5,167,139
[45] Date of Patent: Dec. 1, 1992

[54] DEVICE AND METHOD FOR ASSESSING THE APTITUDE THAT A BODY HAS IN OPPOSING THE PASSAGE OF A PRODUCT AND APPLICATION THEREOF TO DYSMIGRATION ASSESSMENT

[75] Inventors: Eric Lafargue, Paris; Jean Espitalie, Le Vesinet; Thierry Lesage, Tessancourt sur Aubette, all of France

[73] Assignee: Institut Francais du Petrole, Rueil-Malmaison, France

[21] Appl. No.: 635,250

[22] Filed: Dec. 28, 1990

[30] Foreign Application Priority Data

Dec. 28, 1989 [FR] France ................. 89 17519

[51] Int. Cl.$^5$ ............................................. G01N 15/08
[52] U.S. Cl. ............................................. 73/38
[58] Field of Search ............................................. 73/38

[56] References Cited

U.S. PATENT DOCUMENTS

| | | | |
|---|---|---|---|
| 2,498,198 | 2/1950 | Beeson | 73/38 |
| 2,676,485 | 4/1954 | Morgan | 73/38 |
| 2,724,963 | 11/1955 | Ten Brink | 73/38 |
| 3,023,606 | 3/1962 | Sarem | 73/38 |
| 3,139,747 | 7/1964 | Ferrell et al. | 73/38 |
| 3,181,346 | 5/1965 | Davies | 73/38 |
| 4,253,327 | 3/1981 | Wiley | 73/38 |

FOREIGN PATENT DOCUMENTS

| | | | |
|---|---|---|---|
| 2650643 | 9/1978 | Fed. Rep. of Germany | 73/38 |
| 229002 | 2/1969 | U.S.S.R. | 73/38 |

Primary Examiner—Hezron E. Williams
Assistant Examiner—Joseph W. Roskos
Attorney, Agent, or Firm—Antonelli, Terry, Stout & Kraus

[57] ABSTRACT

A method and device are disclosed for assessing the aptitude that a body has in opposing the passage of a fluid product, the method includes the following steps: the body is placed between two reservoirs, one being a transmitter containing the product and the other being a reservoir receiving the part of the product passing through the body, the body separating the reservoirs and being adjacent each of them, a pressure gradient is formed between the reservoirs, this gradient causing the movement towards the receiving reservoir of at least a part of the product contained in the reservoir transmitting through the body, and the part of the product recovered in the reservoir is analyzed.

17 Claims, 1 Drawing Sheet

DEVICE AND METHOD FOR ASSESSING THE APTITUDE THAT A BODY HAS IN OPPOSING THE PASSAGE OF A PRODUCT AND APPLICATION THEREOF TO DYSMIGRATION ASSESSMENT

BACKGROUND OF THE INVENTION

The present invention relates to the assessing of the aptitude that a body has in opposing the passage of a product. It applies particularly well to roof rocks of natural oil deposits. The aptitude of a roof rock to oppose the passage of hydrocarbons is an essential parameter in the oil-bearing assessment of geological formations. A good roof rock will oppose the passage of hydrocarbons whereas a poor roof rock will let hydrocarbons readily pass therethrough. At the present time there exists no means for defining this property in a simple and reliable way. The present invention provides a method and device for classifying roof rocks in particular as a function of their aptitude to oppose the passage of hydrocarbons under the conditions of a dysmigration test carried out in the laboratory on rock samples. By dysmigration is meant the physical phenomenon of the leaking of a product such as hydrocarbons from a reservoir through a roof rock.

SUMMARY OF THE INVENTION

Thus, generally, the present invention relates to a method for assessing the aptitude that a body has in opposing the passage of a product. This method comprises the following steps:

said body is placed between two reservoirs, one being a transmitter containing the product and the other being the reservoir receiving the part of the product passing through said body, said body separating said reservoirs and being adjacent each of them.

a pressure gradient is formed between said reservoirs, this gradient causing the movement towards said receiving reservoir of at least a part of said product contained in the reservoir transmitting through said body, and the part of the product recovered in said reservoir is analyzed.

The analysis of the part of the product recovered in said receiving reservoir may be carried out by continuously sweeping said reservoir.

The method of the present invention may comprise a step for pressurizing said body accompanied, as required, by an operation for heating said body.

The above mentioned analysis may be a qualitative and/or quantitative analysis of the recovered part of said product.

The method according to the invention may comprise the determination of a dysmigration criterion with respect to the volume of said body.

The method and device according to the invention may be applied to assessing the dysmigration of a hydrocarbon through a rock sample. They may simply be applied to assessing the dysmigration of a product other than hydrocarbons, particularly water, carbon monoxide, carbon dioxide or sulfur dioxide.

The present invention also relates to a device for assessing the aptitude that a body has in opposing the passage of a product, said device comprising a high pressure enclosure itself comprising a confinement medium, and means for generating a confinement pressure.

It further comprises an assembly, or test cell, hermetically isolated from the confinement medium, said assembly comprising a sample of said body and two reservoirs, one transmitting which contains said product and the other receiving for recovering the part of the product passing through said sample, said reservoirs being placed on each side of said sample and being adjacent said sample.

The device may comprise means for controlling the pressure gradient existing between said transmitting reservoir and said receiving reservoir.

The device may comprise means for sweeping said receiving reservoir.

The sweeping means may comprise means for detecting and/or analyzing the fluids collected by sweeping in said receiving reservoir.

The device of the invention may comprise means for regulating the temperature of the sweeping fluids.

The device according to the invention may comprise principally an enclosure, or high pressure cell, in which an assembly is placed formed by the superimposition or juxtapositioning of a reservoir transmitting a rock sample and a receiving reservoir inside an assembly isolated hermetically from the confinement medium, preferably by means of a metal jacket and two steel plugs. In the rest of this text, this assembly may also be designated by test cell. Under the effect of a pressure gradient between the reservoirs and in the presence of a confinement pressure, the fluids or products contained in the transmitting reservoir move towards the receiving reservoir where a sweeping system may transport them towards specific detectors, for thus continuously analyzing the expelled products.

The originality of the present invention resides, in particular, in the juxtapositioning of the roof rock sample and the reservoirs, on each side of this sample, in an assembly which is hermetic relatively to the confinement medium. In addition, for certain particular embodiments, it further resides in the continuous analysis of the recovered products by means of the sweeping device. In this latter case, it is therefore possible to study the kinetics of the dysmigration through the roof rock, which would not be possible if the cell had to be dismantled after each experiment. Thus, the dysmigration of a gas-liquid mixture through a roof rock may be studied. For example, a gas and liquid hydrocarbon mixture.

Of course, the present invention also allows the aptitude that a body has to be traversed by a product to be characterized.

BRIEF DESCRIPTION OF THE DRAWINGS

The present invention will be better understood and its advantages will be clear from the following description of a particular embodiment of the device according to the invention, which is in no wise limitative, applied to the case of rocks, and illustrated by the accompanying drawings, in which.

DESCRIPTION OF THE PREFERRED EMBODIMENT

Figure 1:
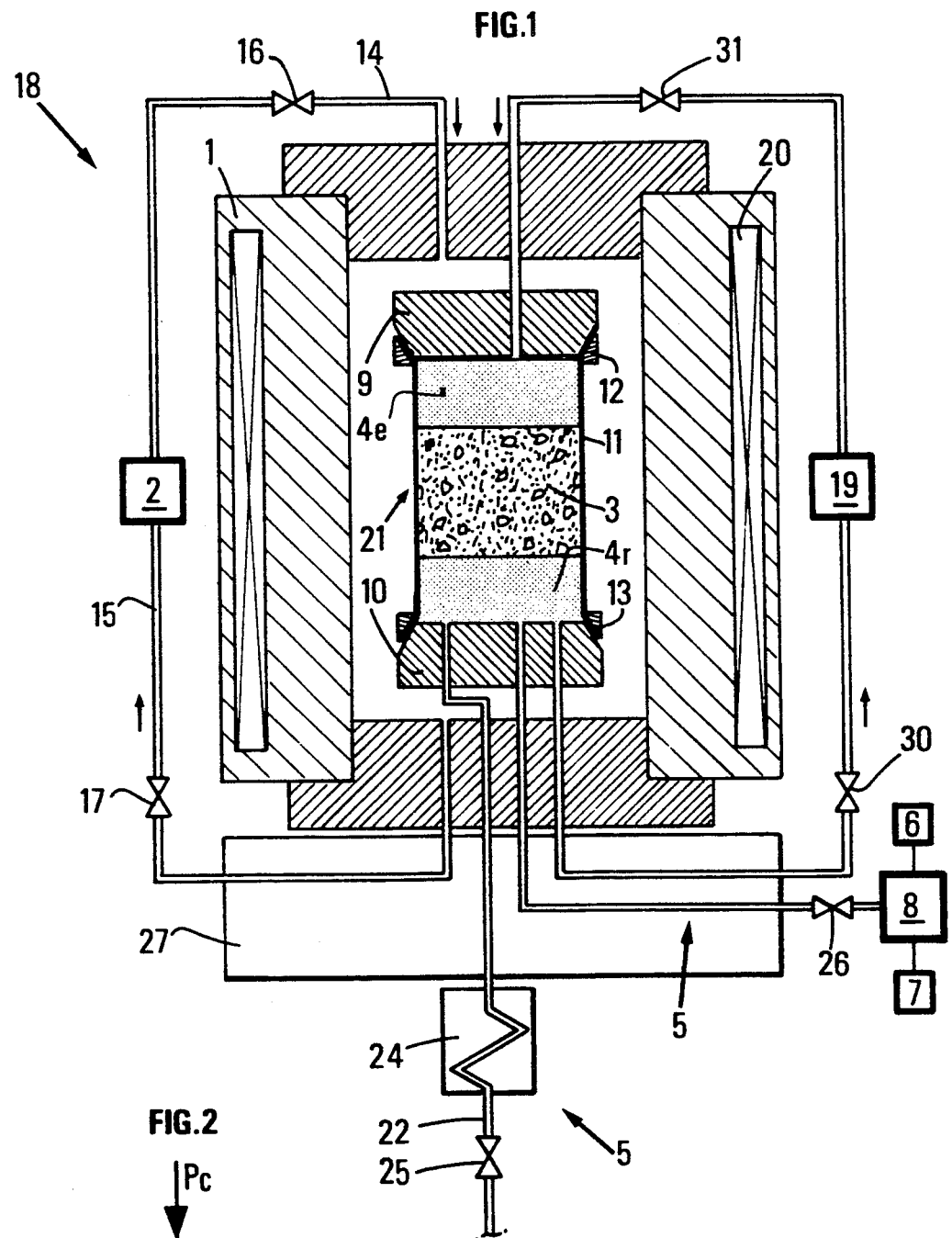
FIG. 1 illustrates as a whole the device of the present invention.

The apparatus illustrated in FIG. 1 comprises:

a high pressure enclosure body 1, equipped with an oven 20, for working at pressures generally between 1 and 4000 bars and temperatures generally between 20° and 400° C., the oven being integrated or not in the body of the enclosure, confinement pressure generation means 2, and an assembly 21 hermetically isolated from the confinement medium during testing, this assembly or test cell receiving the rock sample 3 to be tested and a transmitting reservoir 4e and a receiving reservoir 4r.

The device of the present invention may also comprise:

means for controlling the pressure gradient 18, 19 between the transmitting reservoir 4e and the receiving reservoir 4r, means for sweeping the products 5 recovered in the receiving reservoir 4r, and/or detectors specific to hydrocarbons 6, and possibly to $CO_2$, CO and $H_2O$, 7, connected to a sampling loop 8.

The test cell 21 contains the rock sample 3 and the transmitting 4e and receiving 4r reservoirs which are juxtaposed and isolated from the confinement medium by two metal plugs 9 and 10 and a metal jacket 11 clamped on the preceding elements by two metal rings 12 and 13 possibly having a wedge shaped cross section.

Means for generating a confinement pressure 2 are connected to the enclosure by ducts 14 and 15 which comprise valves 16 and 17. These valves allow the confinement medium to be isolated from the confinement pressure generation means 2 and as required the confinement enclosure to be emptied when the confinement pressure generation means 2 are stopped.

Reference 18 designates as a whole the means for controlling and possibly creating the pressure gradient within test cell 21. These means may comprise a pump and possibly valving means 30, 31, particularly for isolating the internal space of the test cell from pump 19.

Means 18 for controlling the pressure gradient between reservoirs 4e and 4r conventionally comprise a differential pressure sensor connected to a system for regulating the pressure controlling a pneumatic pump. These gradient control means 18 are designated outside the ducts and the valving means by the reference 19. These means 18 are different from the confinement pressure generation means.

The confinement pressure generation means may comprise one or more pneumatic pumps, which are quite conventional, associated with regulation systems connected to a pressure sensor measuring the pressure prevailing in the confinement enclosure.

The sweeping means 5 may comprise a source of sweeping fluid, not shown, and an input circuit 22 bringing the sweeping fluid provided by this source to the receiving reservoir 4r, through plug 10 and an output circuit 23 conveying the pressure to the sampling loop 8, after it has passed through the receiving reservoir 4r.

The input circuit 22 may comprise heating means for heating the sweeping fluid.

The sweeping circuit comprises valves 25 and 26 for interrupting the flow of sweeping fluid.

To prevent condensation in the duct of the output circuit 23 of the sweeping means, it may extend over a great part of its length through a thermostat controlled assembly 27. The other ducts may also partially extend through said thermostat controlled means, as is shown in FIG. 1.

The device of the present invention allows dysmigration tests to be carried out on natural rock roof rock samples, core rock samples or plugs. The diameter of such rock samples may be between 20 and 50 mm for a length also between 20 and 55 mm.

The dysmigration test consists in studying the quantity and possibly the nature and composition of products recovered in the receiving reservoir in time under the pressure and temperature conditions of the test. Reservoirs 4e and 4r may be made from natural rock (sandstone, carbonates, . . . ) or from any porous material (sintered metal, ceramic, . . . ). Their thicknesses may also be equal or not and vary for example between 2 and 20 mm. The receiving reservoir 4r may be empty at the outset or contain a fluid such as air or water, this fluid being preferably different from that contained in the transmitting reservoir. The presence of a fluid in the receiving reservoir makes it possible to control the pressure which prevails therein. In the embodiment shown in FIG. 1, the products recovered in the receiving reservoir 4r are conveyed towards the different detectors 6 and 7 via a sweeping system comprising a heated fluid (inert gases, water with or without surfactants, $CO_2$, organic solvents). The assembly is heated by means of a thermostat controlled system 27, so as to avoid the appearance of cold spots in the output sweeping circuit 23 where the products might condense, thus falsifying the quantitative analyses. At the output of the sampling loop 8, the hydrocarbons, water, CO, $CO_2$ and $H_2S$ are analyzed separately.

The temperature and pressure ranges may be extended from 20° to 400° C. and from 1 to 4000 bars. The pressures and the temperatures may be recorded automatically and may be programmed as a function of time.

As has been mentioned, the experimental device allows the aptitude of a rock in opposing the passage of fluids, particularly hydrocarbons, water, CO, $CO_2$ and $H_2S$ to be determined. It is possible, according to the present invention, to classify the roof rocks as very good roof rocks, not readily letting hydrocarbons pass, in opposition to poor roof rocks which let hydrocarbons pass easily.

It is also possible with the present invention to determine the kinetics of the dysmigration from the continuous analysis of the products recovered in receiving reservoir 4r, which also makes it possible to characterize the aptitude of the rocks tested in letting pass the products accumulated in natural reservoirs as a function of time.

Figure 2:
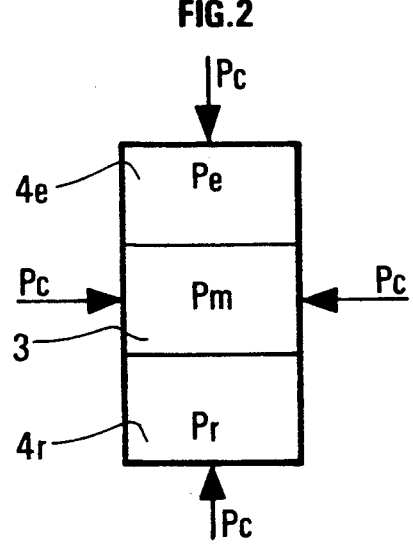
FIG. 2 shows schematically the way in which the pressures are applied to the rock sample and the reservoirs.

FIG. 2 illustrates schematically the pressures to which rock sample 3 and reservoirs 4r and 4e are subjected.

In this figure Pc represents the confinement pressure which is applied to the skeleton of the rock sample 3 and to that of reservoirs 4r and 4e. This pressure Pc corresponds substantially to that which prevails in the enclosure, at least when the resistant force of the metal jacket is negligible with respect to the forces created by the confinement pressure.

Pm designates the pressure in the pores of the roof rock and Pe and Pr designate respectively the pressures prevailing in the pores of the transmitting reservoir and of the receiving reservoir.

The pressure gradient to which the reservoirs are subjected corresponds to the difference: $Pe - Pr$. It is this gradient which makes it possible to cause the fluids to pass through the rock sample 3.

Under normal test conditions, $Pe > Pm > Pr$.

The quantity of fluid initially contained in the transmitting reservoir which has passed through the sample 3 and arriving in the receiving reservoir 4r is studied.

The device according to the present invention allows the quality of roof rocks to be determined.

By way of example, a dysmigration index IDH may be defined proportional or equal to the amount of fluid initially contained in the transmitting reservoir and passing through the rock sample and which is recovered in the receiving reservoir.

To be able to readily compare several samples with each other, it is preferable for the IDH of each of the samples to be determined under identical predetermined test conditions. Thus, the different pressures may be fixed: confinement pressure, pressure in the reservoirs and/or pressure gradient. Similarly, the temperature, the duration, the dimensions of the different component parts of the device and the nature of the reservoirs will be fixed beforehand.

The predetermined confinement pressure Pc may be for example between 1000 and 3000 bars, and the predetermined pressure gradient may be for example between 500 and 2000 bars.

The predetermined temperature of the enclosure may for example be between 50° and 200° C. and preferably between 50° and 150° C.

The time during which the pressure gradient is maintained may for example be between 24 hours and 168 hours and preferably close or equal to 72 hours.

The reservoirs and the rock sample may be cylindrical and have a predetermined diameter, for example between 20 and 50 mm and have a height between 20 and 55 mm.

The ratio of the predetermined volume of the rock sample to that of the transmitting reservoir may be between 0.5 and 1.5, and preferably substantially equal to 1.

The receiving reservoir may have the same form as the transmitting reservoir.

The reservoir may be a natural rock (sandstone, carbonate, porous, volcanic rock, . . . ), a porous synthetic material (sintered metal, ceramic, . . . ).

The jacket may be made from copper.

What is claimed is:

1. Device for assessing the aptitude that a body has in opposing the passage of a product, said device comprising a high pressure enclosure itself comprising a confinement medium, and means for generating a confinement pressure, further comprising an assembly, or test cell, hermetically isolated from the confinement medium, said assembly comprising a sample of said body and two reservoirs, one transmitting which contains said product and the other receiving for recovering the part of the product passing through said sample, said reservoirs being placed on each side of said sample and being adjacent said sample.

2. The device as claimed in claim 1, comprising means for controlling the pressure gradient existing between said transmitting reservoir and said receiving reservoir.

3. The device as claimed in any one of claims 1 and 2, wherein said device comprises means for sweeping said receiving reservoir.

4. The device as claimed in claim 3, wherein said sweeping means comprise means for detecting and/or analyzing the fluids collected by sweeping in said receiving reservoir.

5. The device as claimed in claim 3, comprising means for regulating the temperature of the sweeping fluids.

6. A method for assessing the dysmigration of a rock sample in opposing the passage of fluid material therethrough, which comprises the steps of:

placing said rock sample between two porous reservoirs, one reservoir being a transmitter reservoir containing the fluid and the other reservoir being a receiving reservoir for a part of the fluid passing through said rock sample, said rock sample separating said reservoirs and being positioned adjacent to each of said reservoirs;

forming a pressure gradient between said reservoirs, said gradient causing movement of at least a part of the fluid contained in the transmitter reservoir through said rock sample towards said receiving reservoir; and analyzing the part of the fluid recovered in said receiving reservoir.

7. The method according to claim 6, wherein the part of the fluid recovered in said receiving reservoir is analyzed by continuously sweeping said receiving reservoir with a sweeping fluid.

8. The method according to claim 6 further comprising a step of pressurizing said rock sample together with a step of heating said rock sample.

9. The method according to claim 6, wherein said step of analysis comprises at least one of qualitative and quantitative analysis of the recovered part of the fluid.

10. The method according to claim 9, wherein the dysmigration characteristic of the rock sample is related to the quantity of fluid recovered in said receiving reservoir in relationship to the volume of said rock sample.

11. The method according to claim 6, wherein said fluid is a hydrocarbon and the rock sample is a cap rock covering a reservoir rock of a geological formation.

12. The method according to claim 6, wherein the two porous reservoirs are made of natural rock or a porous permeable synthetic material.

13. A device for determining the dysmigration characteristic of a rock sample in opposing the passage of a fluid therethrough, said device comprising a high pressure enclosure defining a chamber containing a confinement medium, means for generating confinement pressure within said medium; a test assembly hermetically isolated from the confinement medium and located within said enclosure, said assembly comprising said rock sample and two porous reservoirs located on each side of said rock sample; one of said reservoirs acting as a transmitter reservoir for containing said fluid and the other reservoir acting as a receiving reservoir for recovering a part of the fluid passing through said rock sample.

14. The device according to claim 13 further comprising means for controlling the pressure gradient existing between said transmitting reservoir and said receiving reservoir.

15. The device according to claim 13 further comprising means for introducing a sweeping fluid through said receiving reservoir.

16. The device according to claim 15 further comprising means for detecting and/or analyzing fluids collected by the sweeping fluid.

17. The device according to claim 16 further comprising means for regulating the temperature of the sweeping fluid.

* * * * *